(12) United States Patent
Thomas et al.

(10) Patent No.: US 7,118,743 B2
(45) Date of Patent: Oct. 10, 2006

(54) BISPECIFIC MOLECULES CROSS-LINKING ITIM AND ITAM FOR THERAPY

(75) Inventors: David Thomas, Houston, TX (US); Sunny Tam, Missouri City, TX (US)

(73) Assignee: Tanox, Inc., Houston, TX (US)

( * ) Notice: Subject to any disclaimer, the term of this patent is extended or adjusted under 35 U.S.C. 154(b) by 0 days.

(21) Appl. No.: 09/810,883

(22) Filed: Mar. 16, 2001

(65) Prior Publication Data

US 2001/0053770 A1  Dec. 20, 2001

Related U.S. Application Data

(63) Continuation-in-part of application No. 09/440,310, filed on Nov. 17, 1999, now abandoned.

(60) Provisional application No. 60/108,816, filed on Nov. 17, 1998.

(51) Int. Cl.
*A61K 39/395* (2006.01)
*C12P 21/08* (2006.01)
*C07K 16/28* (2006.01)

(52) U.S. Cl. .............................. 424/136.1; 424/143.1; 424/144.1; 424/173.1; 530/387.3; 530/387.1; 530/388.22; 530/388.73

(58) Field of Classification Search ............. 530/387.1, 530/387.3, 388.22; 424/130.1, 133.1, 134.1, 424/135.1, 136.1, 144.1
See application file for complete search history.

(56) References Cited

U.S. PATENT DOCUMENTS

| | | | |
|---|---|---|---|
| 4,179,337 A | 12/1979 | Davis et al. | |
| 4,495,285 A | 1/1985 | Shimizu et al. | |
| 4,609,546 A | 9/1986 | Hiratani | |
| 4,766,106 A | 8/1988 | Katre et al. | |
| 5,225,539 A | 7/1993 | Winter | |
| 5,530,101 A * | 6/1996 | Queen et al. | 530/387.3 |
| 5,534,254 A | 7/1996 | Huston et al. | |
| 5,693,761 A | 12/1997 | Queen et al. | |
| 5,693,762 A | 12/1997 | Queen et al. | |

FOREIGN PATENT DOCUMENTS

| | | |
|---|---|---|
| EP | 0 396 505 A2 | 11/1990 |
| EP | 0 861 891 A1 | 9/1998 |
| WO | WO 96/40788 A1 | 12/1996 |
| WO | WO 98/09638 A1 | 3/1998 |

OTHER PUBLICATIONS

Arm et al. (1997) J. Immunol., vol. 159, 2342-2349.*
Vossebeld et al. (1995) J. Biol. Chem., vol. 270, No. 18, 10671-10679.*
Katz et al. (1997) J. Immunol., vol. 158, 5065-5070.*
Karpovsky, B., Production of Target-Specific Effector Cells Using Hetero-Cross-Linked Aggregates Containing Anti-Target Cell and Anti-Fcγ Receptor Antibodies, *J. Exp. Med.* 160:1686-1701 (1984).
Holgate, S. T., "The role of mast cells and basophils in inflammation", *Clin. Exp. Allergy*, 30(1):28-32 (2000).
Katz, H.R. et al., "Mouse mast cell gp49B1 contains two immunoreceptor tyrosine-based inhibition motifs and suppresses mast cell activation when colligated with the high affinity Fc receptor for IgE", *Proc. Nat. Acad. Sci. USA* 93:10809-10814 (1996).
Evans, M.J. et al., Rapid expression of an anti-human C5 chimeric Fab utilizing a vector that replicates in COS and 293 cells *J.Immunol.*, vol. 184, pp. 123-138 (1995).
Riechmann, L. et al., "Reshaping human antibodies for therapy", *Nature* 332:323-327 (1988).
Katz, H.R. et al., "Activation and Phorbol Ester-Stimulated Phosphorylation of a Plasma Membrane Glycoprotein Antigen Expressed on Mouse IL-3-Dependent Mast Cells and Serosal Mast Cells", *J.Immunol.*, vol. 142(3): 919-926 (1989).
Low, N.M. et al., "Mimicking Somatic Hypermutation: Affinity Maturation of Antibodies Displayed on Bacteriophage Using a Bacterial Mutator Strain", *J. Mol. Biol.* 260:359-368 (1996).
Isakov, N., "ITIMs and ITAMs", *Immunol. Res.*, 16:85-100 (1997).
Huber, M. et al., "The src homology 2-containing inositol phosphatase (SHIP) is the gatekeeper of mast cell degranulation", *Proc. Nat. Acad. Sci. USA* 95:11330-11335 (1998).
Kirshenbaum, A.S. et al., "Effect of IL-3 and Stem Cell Factor on the Appearance of Human Basophils and Mast Cells from CD34+ Pluripotent Progenitor Cells", *J. Immunol.* 148(3):772-777 (1992).
Greenman, J. et al., "Characterization of a New Monoclonal Anti-Fcγ RII Antibody, AT10, and its Incorporation into a Bispecific F(ab')$_2$ Derivative for Recruitment of Cytotoxic Effectors", *Mol. Immunol.* 28(11):1243-1254 (1991).
Lardot, C. et al., "Expression of plasminogen activator inhibitors type-1 and type-2 in the mouse lung after administration of crystalline silica", *Eur. Respir. J.* 11:912-921 (1998).

(Continued)

*Primary Examiner*—Anne Marie S. Wehbé
(74) *Attorney, Agent, or Firm*—Cheryl A. Liljestrand

(57) ABSTRACT

The invention includes bispecific molecules capable of cross-linking ITAM and ITIM receptors on a cell in order to inhibit cell activation, as well as gene therapy approaches using nucleotides encoding such bispecific molecules for expression in vivo. One example of an ITAM/ITIM receptor pair is FcεRI and HM18, and another is FcεRI and FcγRII. Cross-linking of these receptors with a bispecific molecule of the invention would lead to inhibition of the release of allergic mediators and amelioration of the symptoms of allergic diseases. Other diseases can be ameliorated by cross-linking ITIM/ITAM receptor pairs.

10 Claims, 10 Drawing Sheets

OTHER PUBLICATIONS

Leung, D.Y.M., "Molecular Basis of Allergic Diseases", *Mol. Genet. And Metab.* 63:157-167 (1998).

Malbec, O. et al., "Fcε Receptor I-Associated *lyn*-Dependent Phosphorylation of Fcγ Receptor IIB During Negative Regulation of Mast Cell Activation", *J. Immunol.* 160:1647-1658 (1998).

Ochi, H. et al., "T Helper Cell Type 2 Cytokine-mediated Comitogenic Responses and CCR3 Expression During Differentiation of Human Mast Cells In Vitro", *J. Exp. Med.* 190(2):267-280 (1999).

Roche, W. et al., "Subepithelial Fibrosis in the Bronchi of Asthmatics", *Lancet* Mar. 11, 1989, pp. 520-524 (1989).

Renard, V. et al., "Transduction of cytotoxic signals in natural killer cells: a general model of fine tuning between activatory and inhibitory pathways in lymphocytes", *Immunol. Rev.* 155:205-221 (1997).

Sainte-Laudy, J. et al., "Analysis of anti-IgE and allegrgen induced human basophil activation by cytometry. Comparison with Histamine release", *Inflam. Res.* 47:401-408 (1998).

Silibar, C. et al. "Type β Transforming Growth Factors Promote Interleukin-3 (IL-3)-Dependent Differentiation of Human Basophils But Inhibit IL-3-Dependent Differentiation of Human Eosinophils", *Blood* 80(3):634-641 (1992).

Bléry, M et al., "Reconstituted Killer Cell Inhibitory Receptors for Major Histocompatibility Complex Class I Molecules Control Mast Cell Activation Induced via Immunoreceptor Tyrosine-based Activation Motifs", *J. Biol. Chem.* 272(14):8989-8996 (1997).

Daëron, M. et al., "Regulation of High-affinity IgE Receptor-mediated Mast Cell Activation by Murine Low affinity IgG Receptors", *J. Clin. Invest.* 95:577-585 (1995).

Vivier, E. et al., "Immunoreceptor tyrosine-based inhibition motifs", *Immunol. Today* 18(6):286-291 (1997).

Daëron, M., "Building up the family of ITIM-bearing negative coreceptors", *Immunol. Letters* 54:73-76 (1996).

Glennie, M.J. et al., "Preparation and Performance of Bispecific F(ab'γ)$_2$ Antibody Containing Thioether-Linked Fab' Fragments", *J. Immunol.* 139(7):2367-2375 (1987).

Grashoff, W.F.H. et al., "Chronic Obstructive Pulmonary Disease: Role of Bronchiolar Mast Cells and Macrophages", *Am. J. Pathol.* 151(6):1785-1790 (1997).

Daëron, M. et al., "Biology of Immunoreceptor Tyrosine-Based Inhibition Motif-Bearing Molecules", *In:Immunoreceptor Tyrosine Based Inhibition Motifs,* Daëron ed., Chapter 1, Springer (1999).

DiBattista, J.A. et al., "Coordination Regulation of Matrix Metalloproteases and Tissue Inhibitor of Metalloproteinase Expression in Human Synovial Fibroblasts", *J. Rheumatol.* 22(Suppl 43):123128 (1995).

Fleming, T.J. et al., "Negative Regulation of FcεRI-mediated Degranualtion by CD81", *J. Exp. Med.* 186(8):1307-1314 (1997).

\* cited by examiner

FIGURE 5
(A)
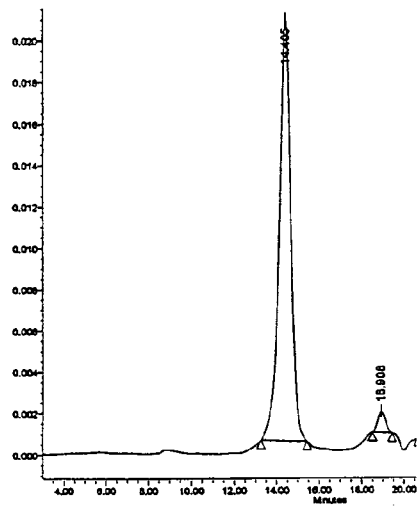
(B)
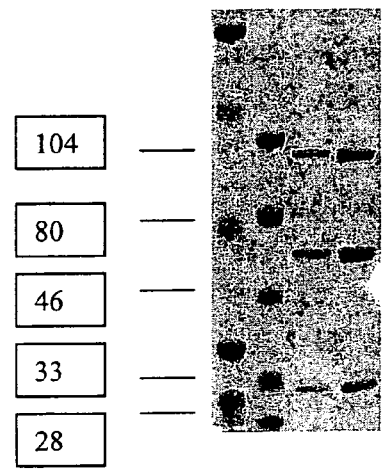

FIGURE 9

BISPECIFIC MOLECULES CROSS-LINKING ITIM AND ITAM FOR THERAPY

This application is a continuation-in-part of U.S. application Ser. No. 09/440,310, filed Nov. 17, 1999 now abandoned, and claims priority under 35 U.S.C. §119e to U.S. Provisional Application No. 60/108,816 filed on Nov. 17, 1998.

BACKGROUND OF THE INVENTION

The immune system is our defense against a variety of antigens, including those associated with bacteria, viruses, and cancerous cells. However, not all immunological responses are beneficial. Allergic diseases including asthma, allergic rhinitis, and atopic dermatitis affect as much as 5 to 10% of the U.S. population. Asthma alone is estimated to affect more than 15 million Americans, with more than 5000 dying annually. More than 10% of children have allergic dermatitis at some point during their childhood (Leung, D., Mol. Gen. and Metab. 63:157–167 (1998). The prevalence of allergic diseases and their associated morbidity has risen dramatically over the last 20 years. Effective therapies that lack deleterious side effects for the management of these diseases are lacking.

Initiation of the immune response involves specific recognition of an antigenic molecule. The immune response is initiated following the binding of antigen to a specific cell receptor. There are a wide variety of receptors, including the T-cell antigen receptor (TCR), the B-cell antigen receptor (BCR), and receptors for the Fc portion of different immunoglobulin subclasses (FCR). One example of an FCR is FcεRI, which binds IgE.

Activation or inhibition of the immune response occurs at the receptor site and involves two different motifs: the immunoreceptor tyrosine-based activation motif (ITAM) and the immunoreceptor tyrosine-based inhibition motif (ITIM). The tyrosine-based motifs undergo rapid, but transient phosphorylation upon receptor ligation, thereby regulating key components of the signaling cascade. ITAMs activate an immune response, whereas the ITIMs inhibit it.

IgE is a well known mediator of the immediate-type hypersensitivity allergic reactions including, e.g., allergic rhinitis ("hay fever"), extrinsic asthma, and food and drug allergies. IgE is secreted by, and expressed on the surface of B-cells or B-lymphocytes. Upon exposure of a mammal to an allergen (antigen), the B-cells specific for that particular antigen are "activated" and develop into IgE-secreting plasma cells. The allergen-specific IgE circulates through the bloodstream. In IgE-mediated allergic reactions, IgE binds through its Fc portion to FcεRI receptors present on the surface of basophils, mast cells, and Langerhans cells. If the IgE bound to the surface of these cells then contacts and binds an allergen, this causes a cross-linking of the bound IgE molecules and hence the underlying receptors, and triggers the release of pharmacologic mediators, such as histamine, serotonin, leukotrienes and the slow-reacting substance of anaphylaxis. These mediators cause the pathologic manifestations of allergic reactions.

Many IgE-mediated allergic conditions or diseases could be inhibited or ameliorated if mast cell activation could be avoided. Cross-linking of an ITAM with an ITIM may cause such a negative regulation of mast cell activation. In fact, it has been demonstrated in animal models that cross-linking of IgE bound to FcεRI (ITAM) with a murine ITIM, gp49 (primarily expressed on the surface of mast cells), inhibits release of mast cell mediators of allergy. International Patent Application WO 98/09638 discusses a rat antibody that targets gp49 (designated mAb B23.1) on the surface of murine mast cells. It was demonstrated that coligation of the FcεRI and gp49 on the surface of mast cells suppresses FcεRI-mediated exocytosis, as evidenced by the release of the secretory granule mediator β-hexosaminidase and the generation of the membrane derived pro-inflammatory lipid mediator leukotriene (LT) C4.

The coligation in this International patent application was accomplished using an F(ab')$_2$ antibody fragment targeting the light chains of both the B23.1 antibody and rat IgE. The mast cells were primed with mAb B23.1 and rat IgE, and then the F(ab')$_2$ fragment was added. Inhibition of exocytosis as compared with controls was evident. This inhibitory effect is believed to be caused by inhibition of the signal transduction cascade that otherwise leads to the release of such mast cell mediators.

Inhibition of mast cell allergic mediators through cross-linking of FcεRI with gp49 (or the human equivalent, HM18) offers new potential treatments for IgE-mediated allergic diseases. Cross-linking of other ITIM and ITAM receptors, which could inhibit activation of a number of cell types carrying these receptors, could provide treatments for a number of diseases and conditions where cellular activation is a disease component, thus providing a much needed therapy for these diseases.

SUMMARY OF THE INVENTION

The present invention relates to bispecfic molecules comprising a first determinant that targets an Immunoreceptor Tyrosine-Based Activation Module (ITAM) and a second determinant that targets an Immunoreceptor Tyrosine-Based Inhibition Module (ITIM). Embodiments of this invention include first a determinant that targets, e.g., IgE, allergen, or FcεRI, as well as a second determinant that targets, e.g., HM18.

Cross-linking of these receptors with a bispecific molecule of the invention would lead to inhibition of the release of allergic mediators and amelioration of the symptoms of allergic diseases. The bispecific molecules of the present invention may include proteins (including peptides), antibodies, or fragments thereof. Antibody fragments may include, e.g., Fab, F(ab')$_2$, and Fv.

One embodiment of the present invention includes pharmaceutical compositions comprising the bispecific molecules of the invention together with a pharmaceutically acceptable carrier, excipient, stabilizer or other additive.

Another embodiment of the present invention relates to methods of treating IgE-mediated allergic diseases and other conditions associated with cell activation, wherein therapeutically effective amounts of the bispecific molecule or a pharmaceutical preparation thereof are administered.

Another embodiment of the present invention relates to gene therapy approaches using nucleotides encoding such bispecific molecules for expression in vivo.

The bispecific molecules may include bispecific antibodies or diabodies, having one determinant derived from an anti-ITAM antibody (including FcεRI) and the other from an anti-ITIM antibody (including HM18). One could also indirectly cross-link the ITAM/ITIM receptors with bispecific molecules binding to molecules that bind to one or to both of these receptors. Examples include a bispecific molecule with one arm binding IgE (which in turn binds to FcεRI) or to an allergen (which is bound by the IgE bound to FcεRI), and the other arm binding to HM18.

A number of different bispecific molecules or antibodies can be used, one example being two single chain Fv antibodies linked together. When administered in vivo, these bispecific molecules bind, directly or indirectly, to an ITAM (e.g., FcεRI) and to an ITIM (e.g. HM18), which are both present on mast cell surfaces. This binding will likely result in the inhibition of cell activation. In the case where the bispecific molecule binds FcεRI and HM18, this would inhibit exocytosis and release of the pharmacologic mediators of allergic diseases.

One embodiment of the bispecific molecules of the invention is formed by conjugating two single chain antibodies, one derived from an antibody specific for an ITAM (e.g., FcεRI) and the other from an antibody specific for an ITIM (e.g., HM18). Another embodiment is a fusion protein including a monoclonal antibody to FcεRI, or a fragment thereof, and an antibody to HM18, or a fragment thereof.

BRIEF DESCRIPTION OF THE FIGURES

FIG. 5A shows HPLC analyses of the bispecific antibody (E.10.10.3×AT.10). and 5B depicts the SDS-PAGE of the antibody electrophoresed on a reduced NuPage Bis-Tris gel (4–12% gradient gel).

FIG. 9 shows the inhibition of histamine release from exogenous IgE by bispecific antibody on human circulating basophils. The leukocyte-enriched fraction of a human buffy coat sample, which included circulating basophils, was treated with human IgE (clone SE44, 10 μg/ml) and then incubated with bispecific antibody at concentrations ranging from 0.03 μg/ml to 100 μg/ml. For comparison, parental antibodies E10.10.3 and AT.10 were also used, as well as anti-DC81. The sample was then challenged with gp120. A biphasic inhibitory pattern was seen, higher concentrations exhibiting a less inhibitory effect than the lower concentrations, and at the lowest concentration (0.03 μg/ml) there is not enough crosslinking to give the same percentage inhibition.

DETAILED DESCRIPTION

Definitions

Figure 1:
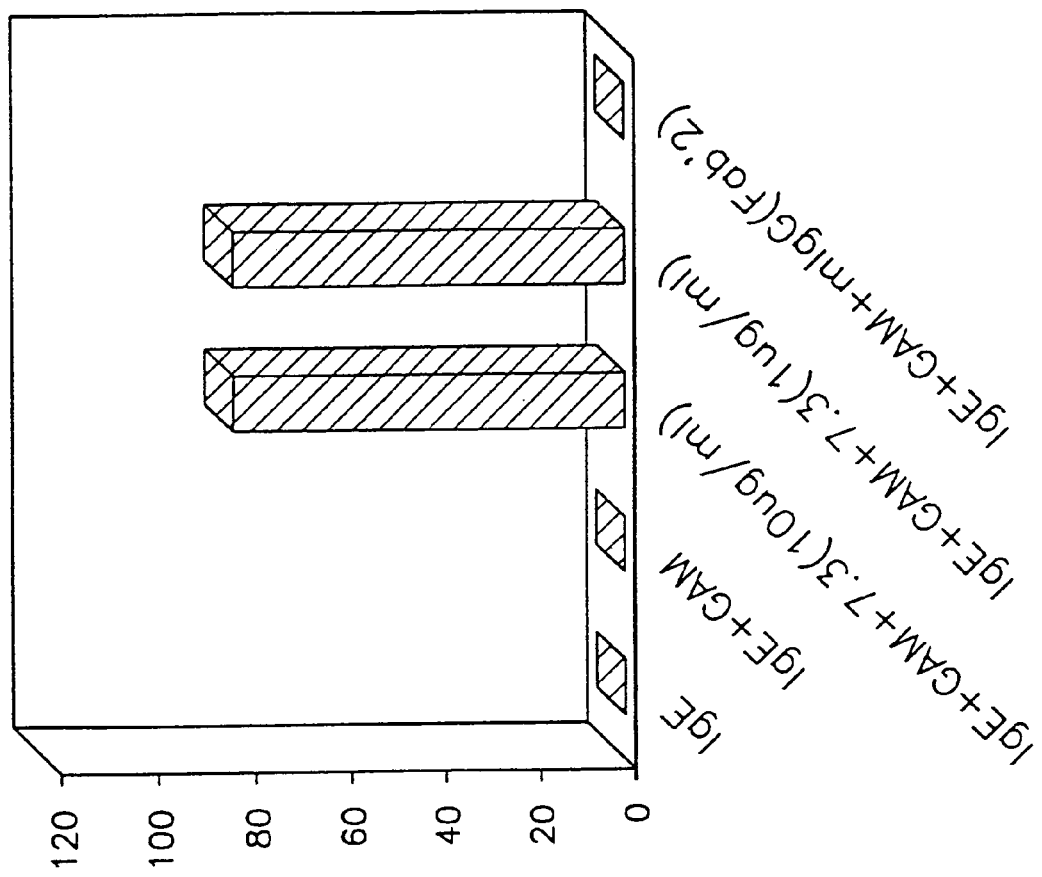
FIG. 1 shows the percentage of inhibition of histamine release from mast cells using GAM (a goat anti-mouse antibody) and 7.3 (a monoclonal anti-human FcγRII antibody) to cross-link FcεRI and FcγRII after IgE binds.

The terms used in this application are intended to be construed with ordinary or typical meaning to those of ordinary skill in the art. Certain terms are given a particular definition below.

Bispecific molecules are intended to include molecules having at least two determinant regions having specificity for a specific ligand. These bispecific molecules can be antibodies including, e.g., monoclonal antibodies, including full-length, polyclonal antibodies, chimeric antibodies, humanized antibodies, deimmunized antibodies, single chain antibodies, and antibody fragments (e.g., Fab, F(ab')$_2$, Fv, and other fragments which retain the antigen binding function of the parent antibody), provided that the antibody exhibits the desired biological activity. Furthermore, the chains of the antibody molecule may be joined by a synthetic linker enabling them to be made as a single protein chain by recombinant methods.

"Humanized" forms of antibodies are antibodies (e.g., murine) comprised of chimeric immunoglobulins, immunoglobulin chains, or fragments thereof, which contain minimal sequences derived from non-human immunoglobulin. In a "humanized" antibody, only the complementarity determining regions (CDRs), which are responsible for antigen binding and specificity, are non-human derived and have an amino acid sequence corresponding to the non-human antibody, and substantially all of the remaining portions of the molecule (except, in some cases, small portions of the framework regions within the variable region) are human derived and have an amino acid sequence corresponding to a human antibody. See, e.g., L. Riechmann et al., Nature; 332: 323–327 1988; U.S. Pat. No. 5,225,539 (Medical Research Council); U.S. Pat. Nos. 5,585,089; 5,693,761; 5,693,762 (Protein Design Labs, Inc.).

"Diabodies" are antibody fragments with two antigen binding sites, comprising a heavy chain variable domain (VH) and a light chain variable domain (VL) in the same polypeptide chain. The domains pair with complementary domains due to a linker that is too short to allow pairing between the two domains of the same chain. Such "diabodies" are described in U.S. Pat. No. 5,534,254 (Creative Biomolecules, Inc.)

In addition to diabodies, it is possible to construct other bispecific molecules capable of coligating HM18 and FcεRI, and suitable for treatment of IgE-mediated allergic diseases in accordance with the teachings of the invention. Such bispecific molecules can be small molecules, antibody homologues or analogues, nucleotides or other molecules capable of coligating HM18 and FcεRI. Such bispecific molecules can be isolated from libraries or otherwise by screening against HM18 and FcεRI, and conducting any further in vitro functional assays, as necessary, including the cellular assays described below.

Methods for Making Antibody Molecules

Techniques for making monoclonal antibodies, single-chain antibodies, etc. can be made by a variety of techniques that are well known in the art. The Human antibodies of the present invention can be made by several different methods, including the use of human immunoglobulin expression libraries (Stratagene Corp., La Jolla, Calif.; Cambridge Antibody Technology Ltd., London, England) to produce fragments of human antibodies ($V_H$, $V_L$, Fv, Fd, Fab, or $(Fab')_2$) and use of these fragments to construct whole human antibodies by fusion of the appropriate portion thereto, using techniques similar to those for producing chimeric antibodies. Human antibodies can also be produced in transgenic mice with a human immunoglobulin genome. Such mice are available from Abgenix, Inc., Fremont, Calif., and Medarex, Inc., Annandale, N.J. In addition to connecting the heavy and light chain Fv regions to form a single chain peptide, Fab can be constructed and expressed by similar means (M. J. Evans et al., J. Immunol. Meth., 184: 123–138 1995). Single chain antibodies ("ScFv") and the method of their construction are described in U.S. Pat. No. 4,946,778.

The antibodies of the present invention are either wholly or partially human and are less immunogenic than wholly murine or non-human-derived antibodies, as are the fragments and single chain antibodies. All these molecules (or derivatives thereof) are therefore less likely to evoke an immune or allergic response. Consequently, they are better suited for in vivo administration in humans than wholly non-human antibodies, especially when repeated or long-term administration is necessary, as may be needed for treatment with the bispecific antibodies of the invention.

U.S. Pat. No. 5,534,254 (Creative Biomolecules, Inc.) describes several different embodiments of bispecific antibodies, including linking single chain Fv with peptide couplers, including Ser-Cys, $(Gly)_4$-Cys, $(His)_6$-$(Gly)_4$-Cys, chelating agents, and chemical or disulfide couplings including bismaleimidohexane and bismaleimidocaproyl. Another embodiment is a dimer having single chain $FvL_1$ and $FvH_2$ linked and $FvH_1$ linked with $FvL_2$. All such linkers and couplings can be used with the bispecific antibodies of the invention.

The bispecific molecules of the invention are administered as a pharmaceutical composition at a dosage effective to inhibit mast cell exocytosis. The effective dosage can be readily determined in routine human clinical trials or by extrapolation from animal models.

Typically, the pharmaceutical composition is administered by injection, intravenously, subcutaneously or intraperitoneally. It may also be possible to obtain compositions which may be topically or orally administered, or which may be capable of transmission across mucous membranes. Preferred routes of administration include oral, dermal, transdermal, and injection.

Before administration to patients, formulants and excipients, well known in the art, are preferably added to the pharmaceutical composition. These substances may be co-administered with the bispecific molecule of the claimed invention, including solvents, dispersion media, delay agents, emulsions, and the like. In addition, additives may include buffering agents, stabilizing agents, preservatives, non-ionic detergents, antioxidants, and other miscellaneous additives (Remington's Pharmaceutical Sciences, $16^{th}$ ed., A. Osol. (1980). Additionally, pharmaceutical compositions can be chemically modified by covalent conjugation to a polymer to increase their circulating half-life. Polymers, and methods to attach them to peptides, are shown in U.S. Pat. Nos. 4,766,106; 4,179,337; 4,495,28; and 4,609,546, and include polyoxyethylated polyols and PEG.

Making monoclonal antibodies against mouse gp49 (the mouse counterpart of HM18) is described in Katz et al., 1989, J. Immunol. 142:919–926. Monoclonal antibodies against human HM18 would be made using analogous methods and techniques, with the human HM18 polypeptide described in International Patent Application WO 98/09638 as the immunogen. Monoclonal antibodies against FcεRI can be made using similar techniques, using a recombinant peptide representative of the sequence of the receptor. These peptides can be linked to a carrier, for example, keyhole limpet hemocyanin, to increase the immunogenicity and the production of antibodies to the immunogen.

Following production of antibody candidates, the antibodies would be screened against mast cells bearing HM18 and FcεRI or against recombinant versions of these receptors. Similar techniques could be used to generate bispecific antibodies capable of indirectly cross-linking HM18 and FcεRI, e.g., bispecific antibodies with one arm binding to IgE or an allergen, and the other arm binding to HM18.

Bispecific antibodies against other ITAM/ITIM receptor pairs (or which are capable of indirectly cross-linking such ITAM/ITIM receptor pairs) could be made using similar techniques, with an appropriate ITAM and ITIM used as immunogens for the mice. The antibody candidates would be screened against the receptor pair, or, if appropriate, the indirect linker(s).

Other bispecific molecules, including peptides, DNA, RNA, other organic molecules or homologues or analogues thereof, can also be made against any ITAM/ITIM receptor pair, or, an indirect linker(s) thereto. Activating receptors include BCR, FcγRI, FcγRIIA, FcαRI, FcγRIIIA and TCR. These ITAM receptors are carried on a variety of human cells and could therefore be regulated by interaction with the appropriate ITIM receptor. The bispecific molecule candidates can then be screened for binding to the designated ITAM/ITIM receptor pair, or the indirect linker(s), using conventional procedures.

One can also express any of the diabodies of the invention, or other bispecific proteins of the invention, with gene therapy techniques. Gene constructs that direct the expression in vivo of the diabodies or bispecific proteins can be administered by an appropriate vector system, including a retrovirus, an adenovirus, a parvovirus or any other vector permitting cellular transfer of the gene constructs, or by incorporation of the gene construct into liposomes with or without the viral vector. In the alternative, such nucleotides can be used to transfect cells ex vivo, using known methods including electroporation, calcium phosphate transfection, microinjection, or incorporation of the gene constructs into liposomes followed by transfection. The cells are then introduced into the patient for expression in vivo. Use of gene therapy for antibody expression is well known in the art. See, e.g., International Patent Application No. WO 98/31808.

The bispecific molecules of the claimed invention may also be subjected to further modifications, depending on the intended use of the molecule. Such modifications can include, further alteration of the amino acid sequence, fusion with heterologous proteins, or other covalent modifications.

EXAMPLE I

Generation of Single Chain Antibody Fragments from Monoclonal Antibodies to HM18 and to FcεRI.

The techniques described in this Example I can be used to generate a single chain antibody fragment (ScFv) of either the anti-HM18 or anti-FcεRI monoclonal antibodies.

Both the $V_H$ and $V_L$ region of the antibodies are amplified by PCR, followed by a second assembly PCR to connect both regions. Four primers are designed. The first contains a HindIII and SfiI restriction site for cloning purposes followed by a degenerated sequence annealing to the 5' $V_H$ region. The second contains a degenerate sequence for the 3' part of the $V_H$ region followed by a sequence encoding a $((Gly)_4Ser)_3$ linker and the 5' part of the $V_L$ regions. The third is a degenerated primer having homology with the 5' part of the $V_L$ region, while the last primer contains a NotI restriction site and anneals to the 3' part of the $V_L$ region.

As a template for this PCR reaction, one can use a plasmid containing the $V_H$ or $V_L$ regions of the antibody of interest. The cDNA obtained in this PCR step is gel purified and used in an assembly PCR resulting in the linkage of the V region through the $((Gly)_4Ser)_3$ linker. Subsequently the single chain construct obtained is digested with the restriction enzymes HindIII and NotI, followed by ligation in pGEM-13Zf (Promega, Madison, USA). The ligation is transformed in DH5α and plated on LB plates. By sequencing of several clones, a correct ScFv clone is found.

EXAMPLE II

Construction of Bispecific Diabody Molecules Capable of Binding to HM18 and FcεRI Bispecific bivalent molecules can be generated by shortening the flexible linker sequence in the anti-HM18 ScFv and in the anti-FcεRI ScFv, from fifteen residues to five ($Gly_4Ser$) and by cross-pairing the variable heavy and light chain domains from the two single chain Fv fragments with the different antigen recognition. The construction is preferably performed in three steps. The light chain variable fragments are exchanged in the ScFv constructs from an anti-HM18 ScFv and an anti-FcεRI ScFv by using restriction enzyme sites located in the 5'-end and just outside the 3'-part of the light chain variable gene. In the following step, the 15-residue linker of the chimeric construct $V_H$-a HM18/15AA-linker/$V_L$-a-FcεRI is replaced by the 5 residue linker ($Gly_4Ser$) by using sites located in the 3'-part of $V_H$ and the 5'-part of $V_L$. Finally, a chimeric cassette is combined in the vector pUC119-fabsol (a pUC119 derivative similar to pUC119His6mycXba (Low et al., *J. Mol. Biol.* 260:359 (1996)), but with all ApaII-sites in the vector backbone deleted by in vitro mutagenesis) containing a bi-cistronic expression cassette. A diabody-producing clone containing both ScFv-cassettes is identified and used for expression of the recombinant diabody molecule.

EXAMPLE III

Cellular Assays to Screen for Non-Activating High Affinity Antibodies Against IgE or FcεRI Receptor and HM18 Antibodies Human FcεRI receptor (Invitrogen Inc. or Beth Israel Hospital) and human HM18 receptor (Brigham & Women Hospital) can be co-transfected into the rat mast cell line, RBL-2H3 (ATCC collection). Briefly, transfected cells are resuspended in RPMI 1640 medium supplemented with 10% FCS at $1\times10^6$ cells/ml and incubated at 37° C. for 1 hour with 2 μCi/ml [$^3$H] serotonin (Amersham Corp.). The cells are washed and reincubated for another hour at 37° C. and transferred to 96-well microculture plates at $2\times10^5$ cells/well. Cells are then treated with individual bispecific hybridoma supernatant or carrier coupled diabody specific for human FcεRI and HM18 receptors and left for 1 hour. Before challenge with human IgE and IgE crosslinking reagent for 30 minutes, the attached cells are washed and warmed for 15 minutes at 37° C. Reactions are terminated by adding 50 μl of ice-cold medium and by placing plates on ice. 50 μl of supernatants are mixed with 1 ml of emulsifier safe scintillation liquid and counted in a Beckman counter. The percentage of serotonin release is calculated using as 100% the cpm obtained from the same number of pulsed cells lysed in 0.5% SDS and NP-40. The diabodies that can inhibit maximum serotonin release would be the choice for further characterization.

For further testing of the selected diabody constructs, a secondary confirmatory human cord blood derived mast cell culture could be used. Briefly, cultured human mast cells can be raised from commercially available CD34+ purified human umbilical cord blood mononuclear cells through the addition of 80 ng/ml of rhSCF, 50 ng/ml rhIL-6 and 5 ng/ml rhIL-10 for 6 to 8 weeks. The confirmed mast cell population after FACS sorting will be plated into 96-well microculture plates. Cells are then treated with selected diabody supernatants for 1 hour. Before challenge with human IgE and IgE crosslinking reagent for 30 minutes, the cells are washed and warmed for 15 minutes at 37° C. The histamine release into the media is measured with the ELISA detection system from Immunotech, Inc. The diabodies that can inhibit maximum histamine release would be the choice for further characterization.

EXAMPLE IV

Reduction of Mast Cell Degranulation by Cross-Linking of the ITIM and ITAM Receptors A monoclonal anti-human FcγRII antibody, clone 7.3, significantly diminished IgE induced human mast cell degranulation by more than 90% when the IgE receptor is crosslinked to the inhibitory FcγRII receptor by the goat anti-mouse antibody (GAM). This is illustrated in the amount of histamine released from the IgE+GAM group versus the IgE+GAM+7.3 group. An isotype matched mouse IgG Fab'$_2$ was used as a control, showing the importance of crosslinking the inhibitory receptor FcγRII to the IgE receptor (see FIG. 1). The experiment is described briefly below.

CD34+ cells were isolated from human cord blood using Dynal CD34 coated beads. The isolated cells were cultured in the presence of 80 ng/ml of recombinant human stem cell factor, 50 ng/ml of recombinant human interleukin 6 and 5 ng/ml of recombinant human interleukin 10 for about 8 weeks. For each group, $1\times10^5$ human mast cells were treated with mouse IgE (10 μg/ml), mouse IgE+mouse anti-human FcγRII antibody, clone 7.3 (1 or 10 μg/ml), or isotype matched mouse IgG Fab'$_2$ (10 μg/ml) for the first hour of incubation at 37° C. Subsequently, the cells were washed twice with PBS before applying the goat anti-mouse Fab'$_2$ (GAM, 10 μg/ml) to the selected groups for another hour of incubation at 37° C. The histamine release into the supernatant from each treatment group was tested with the human histamine ELISA kit from Immunotech, Inc.

FIG. 1 shows histamine release inhibition of human cord blood mast cells upon crosslinking of FcεRI and FcγRII receptors. The percentage of inhibition was the comparison of the amount of histamine release (in nM) between the crosslinked groups versus the positive control group (IgE+GAM) in lane 2 in FIG. 1.

EXAMPLE V

Mast Cell Inhibition with a Bispecific Rabbit IgG

Additional cellular experiments of the ITAM/ITIM concept were done with two forms of antibodies: 1) a bispecific single antibody; 2) a presumably bispecific rabbit IgG.

Crosslinking of FcεRI (ITAM) and FcγRII (ITIM) on a mouse mast cell line, C-57, using a presumably bispecific rabbit IgG, confirmed the significance of ITAM/ITIM receptor co-ligation in repressing mouse mast cell activation and degranulation in a dose dependent manner (ranging from 20% to 74% inhibition). The variable region of the rabbit IgG could recognize the FcεRI via the antigen (DNP-HSA), and the Fc region predominantly only targets the FcγRII and RIII family receptors.

The protocol was that mouse mast cells ($2 \times 10^5$ cells/group) were incubated with IgE anti-DNP (1 μg/ml) for 45 minutes at 37° C. DNP-HSA (5 ng/ml) was incubated with rabbit IgG anti-HSA (at various concentrations, ranging from 0.01 to 100 μg/ml) for 15 minutes at 37° C. After washing the treated cells with Tyrode's buffer, cells were incubated with the IgG complexed antigen for another 45 minutes at 37° C. The β-hexosaminidase activity released into the supernatant was measured by the hydrolysis of pNpp.

Figure 2:
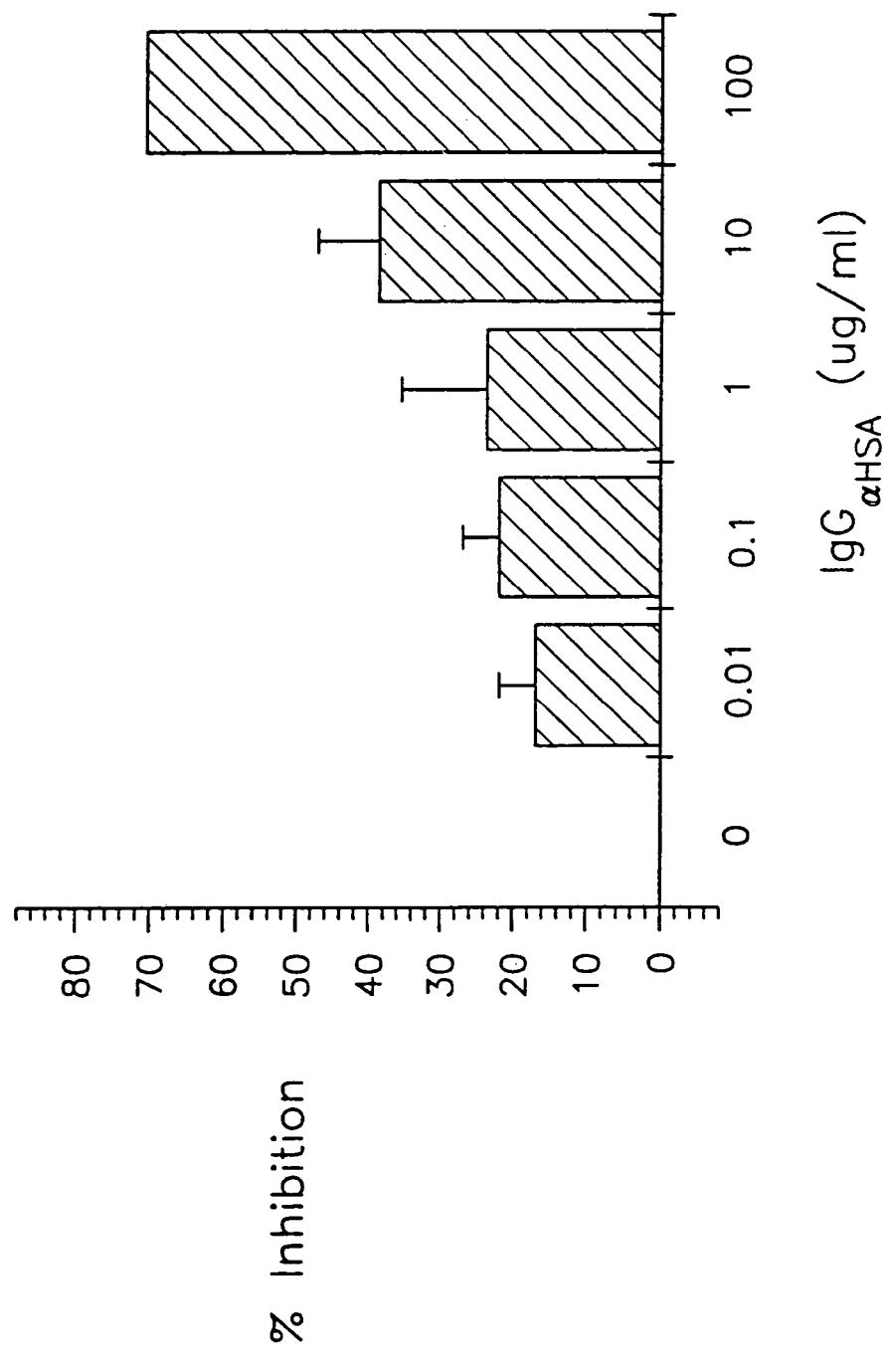
FIG. 2 shows the inhibition of β-hexosaminidase release from C57BL/6 mouse mast cells upon crosslinking of FcεRI and FcγRII receptors by a polyclonal rabbit IgG anti-HSA.

FIG. 2 shows the Inhibition of β-hexosaminidase release from C57BL/6 mouse mast cells upon crosslinking of FcεRI and FcγRII receptors by a rabbit IgG anti-HSA. The percent of inhibition was the comparison of the amount of β-hexosaminidase release (in nM) between the crosslinked groups (lanes 2 through 6) versus the positive control group (IgE+DNP-HSA, lane 1).

EXAMPLE VI

Inhibition with Another Bispecific Antibody

A chemically conjugated bispecific multivalent antibody that targets the di-nitrophenyl moiety (DNP) and mouse FcγRII/III receptors (clone 2.4G2) was obtained. Using this molecule at the optimal concentration of 1 μg/ml, a 50% inhibition of β-hexosaminidase release was demonstrated. At higher concentrations of 2.4G2-anti-DNP, such as 10 to 100 μg/ml, the inhibition is diminished. This diminished inhibition is likely due to increases in crosslinking of the activatory receptors in addition to the inhibitory receptor, FcεRII B.

The protocol for this experiment was that mouse mast cells ($2 \times 10^5$ cells/group) were incubated with IgE anti-DNP (1 μg/ml) both with and without 2.4G2-anti-DNP (at various concentrations, ranging from 0.1 to 100 μg/ml) for 45 minutes at 37° C. After washing with Tyrode's buffer, cells were incubated with the antigen, DNP-HSA (5 ng/ml) for another 45 minutes at 37° C. The β-hexosaminidase activity was measured by the hydrolysis of pNpp.

Figure 3:
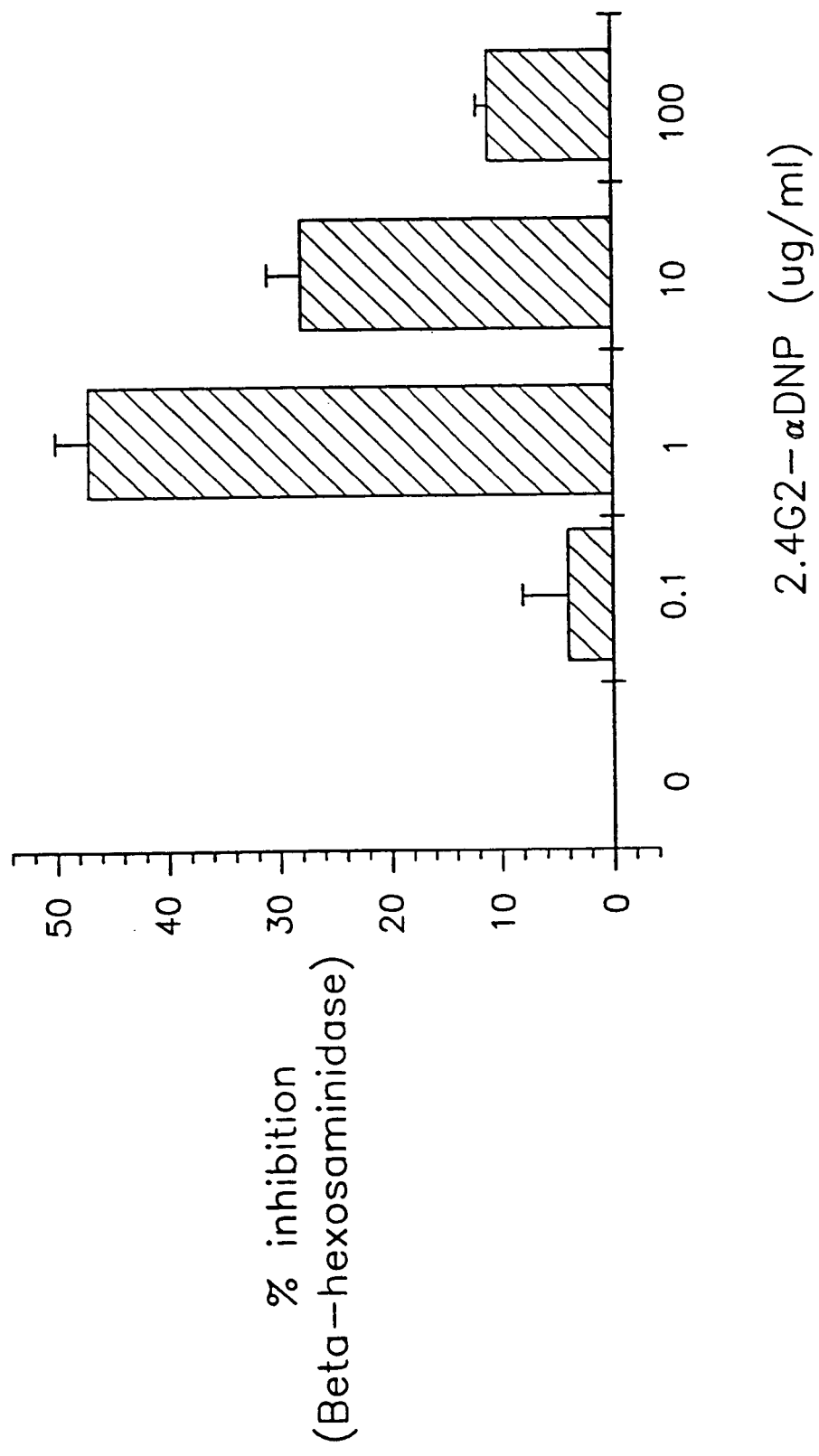
FIG. 3 shows the inhibition of β-hexosaminidase release from C57BL/6 mouse mast cells upon crosslinking of FcεRI (which IgE bound to DNP is absorbed) and FcγRII/RIII receptors by a bispecific 2.4G2-anti-DNP antibody.

FIG. 3 shows the inhibition of β-hexosaminidase release from C57BL/6 mouse mast cells upon crosslinking of FcεRI and FcγRII receptors by a bispecific 2.4G2-anti-DNP antibody. The percent of inhibition was the comparison of the amount of β-hexosaminidase release (in nM) between the crosslinked groups (lanes 2 through 5) versus the positive control group (IgE anti-DNP+DNP-HSA, lane 1).

EXAMPLE VII

Inhibition with a Passive Cutaneous Anaphylaxis Model

The ITAM/ITIM concept has been well documented with cellular models in the literature and demonstrated with human cultured mast cells, as described in Examples I to III. To demonstrate the impact and feasibility of aggregation of the ITAM/ITIM receptors in animals, the Segal's bispecific molecule was applied in a passive cutaneous anaphylaxis (PCA) animal model.

Using this model, a 30% to 40% inhibition of the anaphylactic response was demonstrated. Given the 2.4G2 antibody also recognizes many activatory RII and RIII receptors, this experimental data shows the dominance of the inhibitory receptors in vivo and the feasibility of the ITAM/ITIM crosslinking as a therapeutic. The protocol was that the surface of the left ear of anesthetized Balb/c female mice (4 to 5 weeks old) were injected with 25 ng of anti-DNP IgE, and the right ear was injected with 25 ng of anti-DNP IgE plus the appropriate dose of the bispecific antibody (ranging from 0.25 to 1 μg/mouse). After 24 hours, 100 μg of DNP-HSA in 2% Evan's blue/PBS was delivered via the tail vein. Control animals (group 1) received only IgE in the left ear and the bispecific antibody alone in the right ear. After injecting the antigen for 45 minutes, the mice were sacrificed by cervical dislocation/$CO_2$. For quantification of the Evan's blue dye extravasation, the ears were removed, minced and incubated at 80° C. for 3 hours in 2 ml of formamide. The absorbance values were read at 610 nm and the standard deviation was calculated for each group of at least 3 animals.

Figure 4:
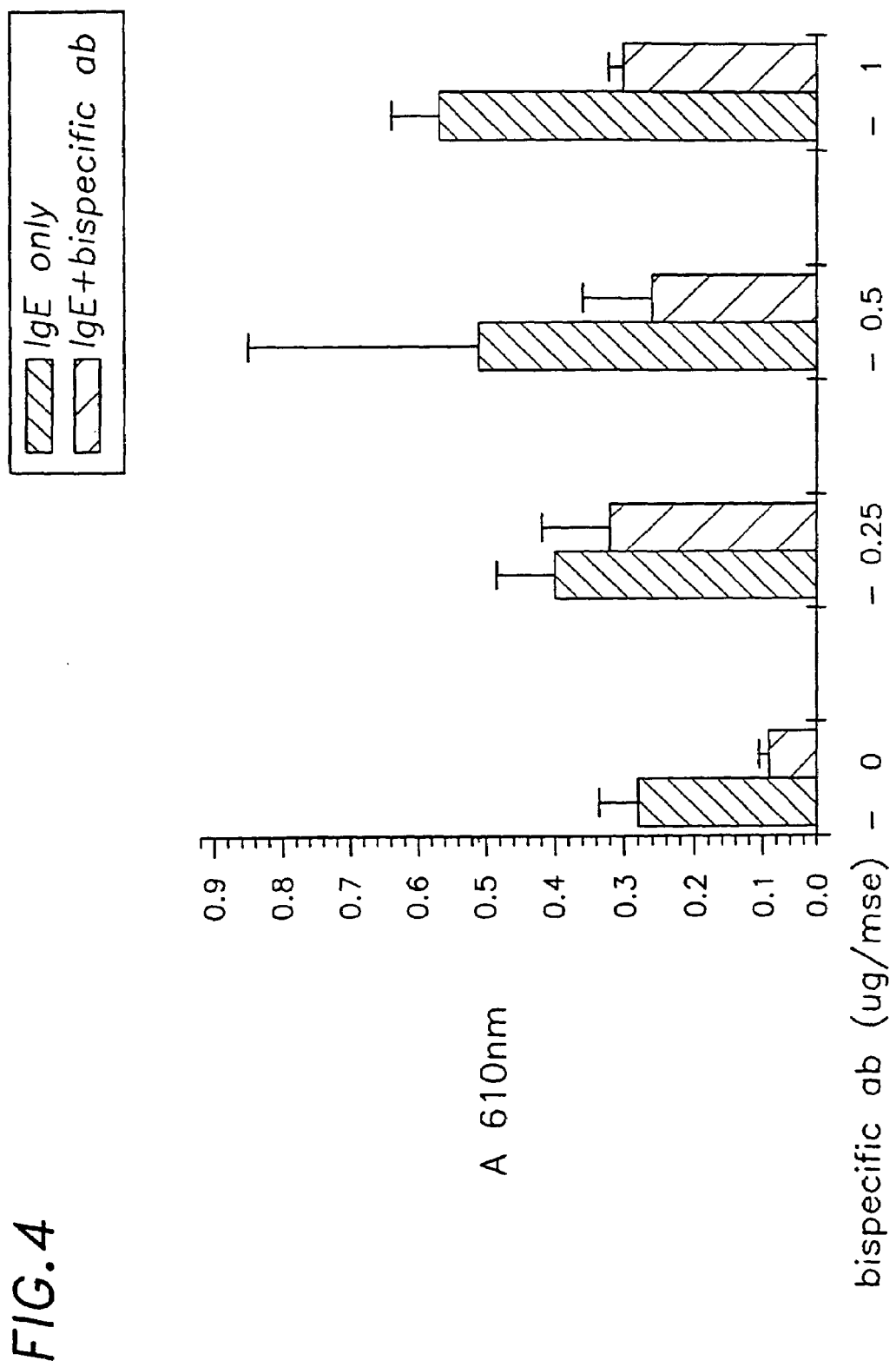
FIG. 4 shows the inhibition of passive cutaneous anaphylaxis in Balb/c mice upon crosslinking of FcεRI and FcγRII receptors by a bispecific 2.4G2-anti-DNP antibody. IgE was added at increasing doses, as shown.

FIG. 4 shows the results, where inhibition of passive cutaneous anaphylaxis in Balb/c mice upon crosslinking of FcεRI and FcγRII receptors by a bispecific 2.4G2-anti-DNP antibody.

EXAMPLE VIII

Chemically Conjugated Bispecific ITAM/ITIM Antibody

A bispecific chemically conjugated antibody having antigen binding regions from a mouse anti-human IgE (clone E.10.10.3) and a mouse anti-human FcεRII (clone AT.10) was constructed using the chemical linker, o-phenylenedimaleimide, to conjugate the antigen binding regions.

Figure 10:
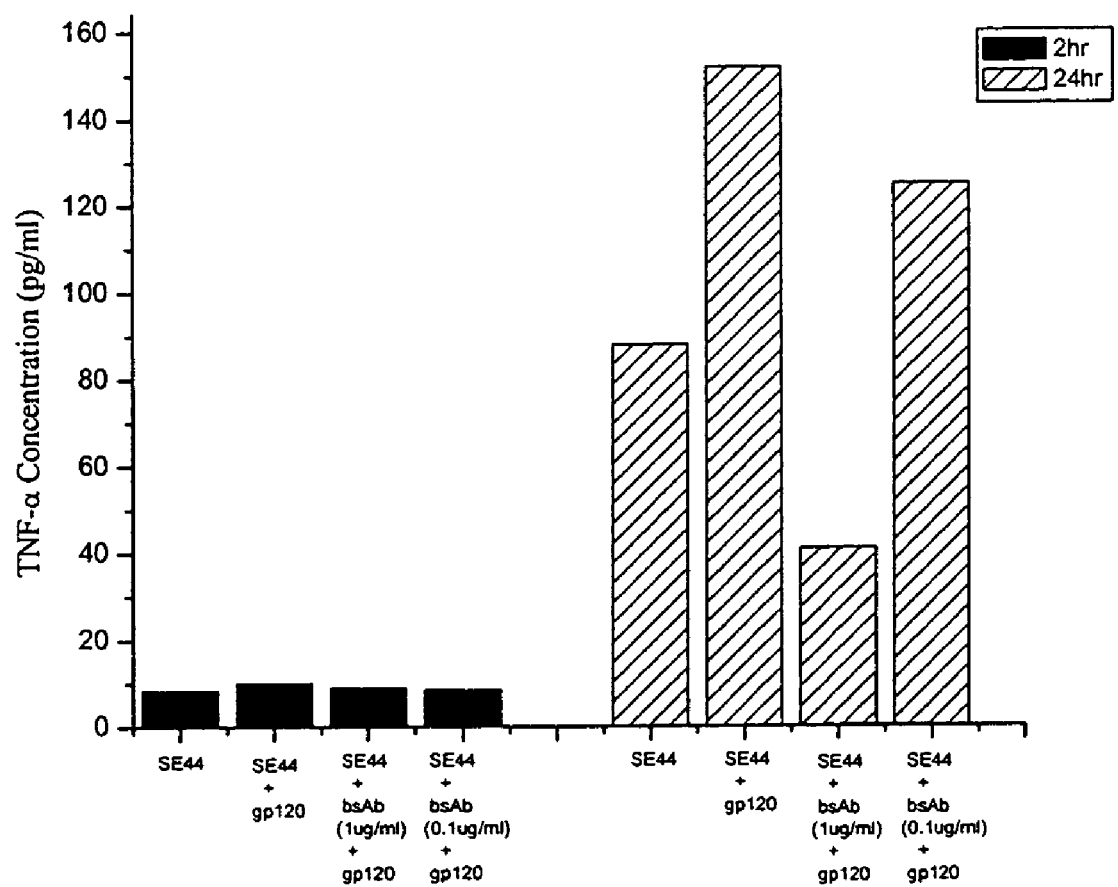
FIG. 10 shows the inhibition of TNF-α release by bispecific antibody on human cultured mast cells. Cultured mast cells were first treated with IgE (clone SE44, 10 μg/ml) and then incubated with bispecific antibody at a concentration of 0.1 μg/ml or 1.0 μg/ml or without bispecific antibody. The cells were then challenged with ovalbumin-conjugated gp120 for 2 and 24 hours before TNF-α release was measured. It appears to take 24 hours for TNF-α transcription to take place thus demonstrating inhibition of TNF-α release.

Chromatography analysis with HPLC of the bispecific antibody (E.10.10.3×AT.10) showed a predominant peak at about 100 kilodaltons as compared to the standards (FIG. 5A). In FIG. 5A, 10 μg of the antibody was eluted with a size exclusion column at OD 280 nm. In FIG. 5B, 2.5 μg (lane 3) and 5 μg (lane 4) of the antibody was electrophoresed on a reduced NuPage Bis-Tris gel (4–12% gradient gel). The partially reduced $Fab_2$ molecule exhibited the reduced forms of the molecule consisting of heavy and light chain fragments (FIG. 5B). Lanes 1 and 2 are prestained standards from Bio-Rad Inc. The molecular weights on the left of the gel are expressed in kilodaltons.

Figure 6:
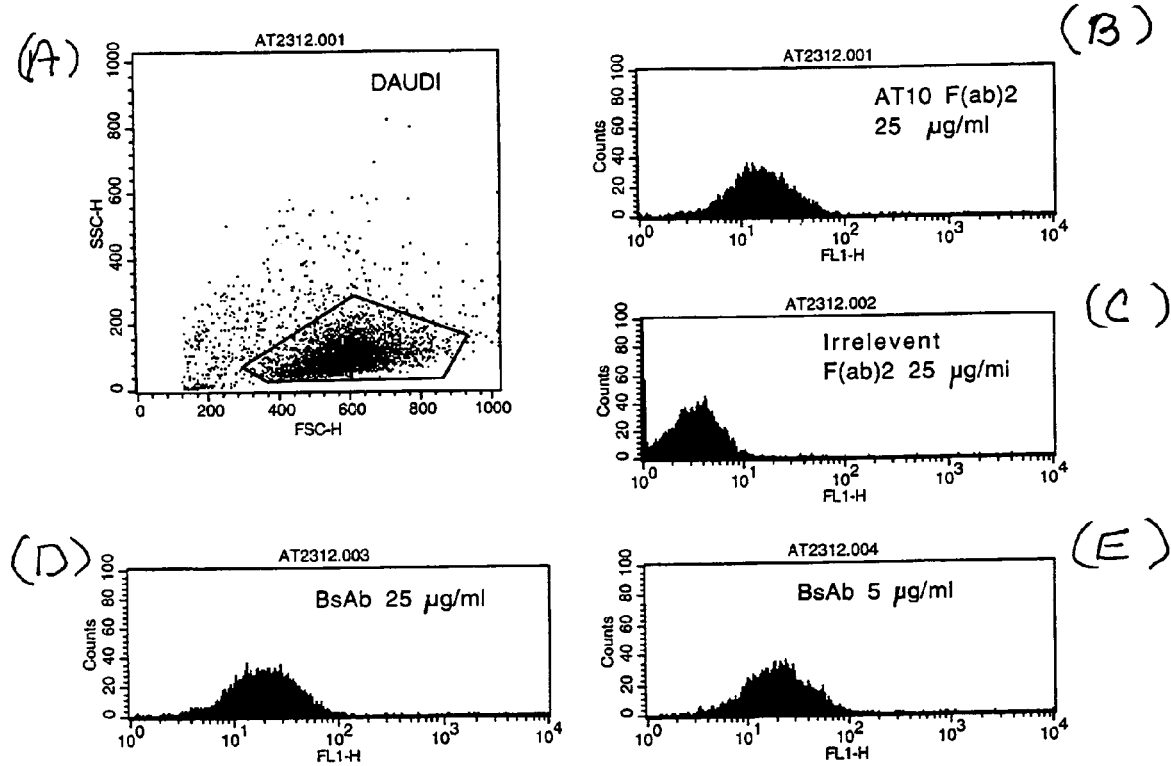
FIGS. 6A–6E show FACS analysis of Daudi cells stained with the bispecific antibody (E10.10.3×AT.10) at 5 μg/ml and 25 μg/ml, one of its parental antibody clones (AT.10), and an irrelevant control antibody.

Further analyses were conducted to demonstrate that the bispecific antibody still retains the original antigenicities as the parental antibodies after the chemical conjugation procedure. First, the bispecific antibody [E.10.10.3×AT.10 F(ab)$_2$] was analyzed using fluorescent antibody cell sorting (FACS) via cellular staining of a Burkitt lymphoma cell line, Daudi (FIG. 6A). The positive staining exhibited by the bispecific antibody at both 5 (FIG. 6E) and 25 µg/ml (FIG. 6D) was similar to the staining exhibited by one of the parental antibodies [AT.10, F(ab)$_2$] (see FIG. 6B). An irrelevant control antibody F(ab)$_2$ did not show positive staining (FIG. 6C). Secondly, the bispecific antibody was tested in an ELISA assay to confirm binding to human IgE coated microtiter plates (data not shown).

Figure 7:
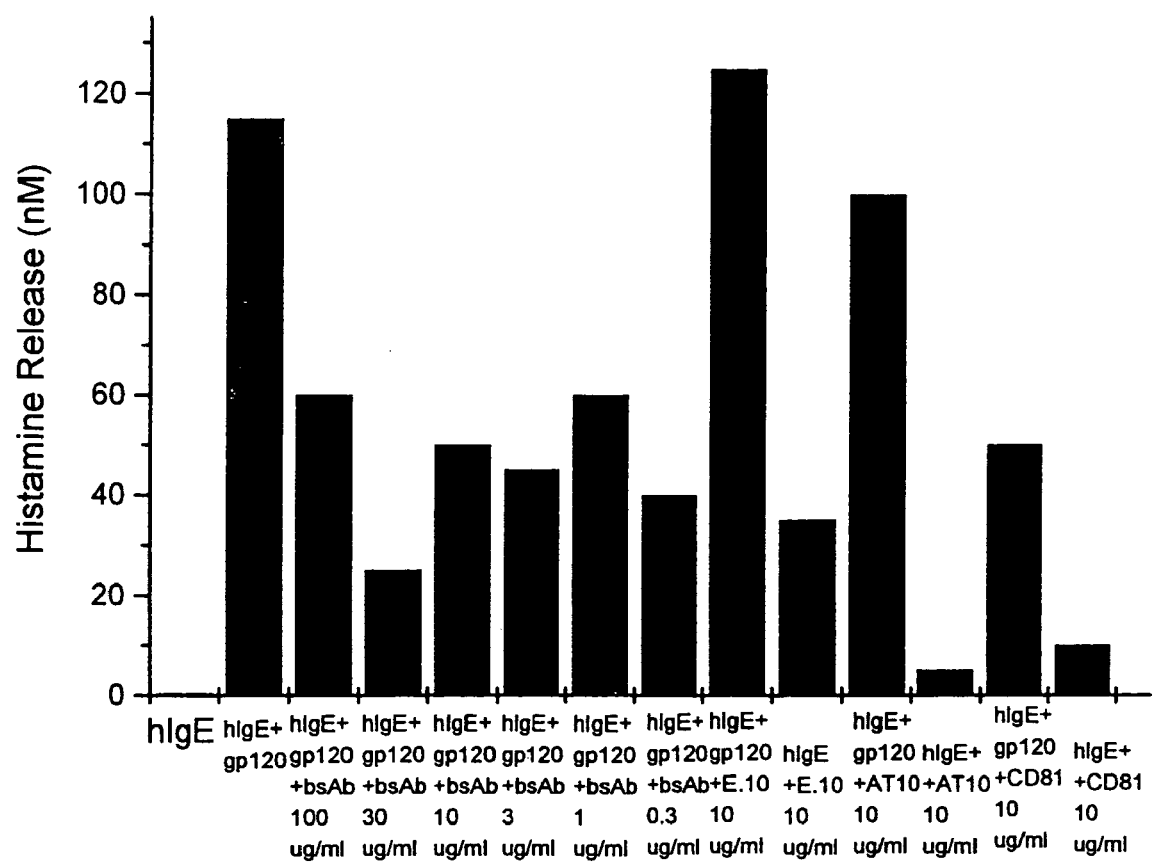
FIG. 7 shows the inhibition of histamine release by bispecific antibody (bsAb) on human cultured mast cells. Mast cells were first exposed to human IgE specific to the viral glycoprotein gp120, and then incubated with the bispecific antibody, E10.10.3, AT.10, or anti-CD81 (a leukocyte cell surface protein). These cells were then challenged with ovalbumin-conjugated gp120 peptide. Inhibition of mast cell degranulation ranged from 50–75%.

The bispecific antibody was then tested in cellular assays using human cultured mast cells and human cultured basophils to demonstrate the inhibition of histamine release. Human CD34$^+$ cells were cultured for 8 to 10 weeks in the presence of 80 ng/ml stem cell factor (SCF), 50 ng/ml IL-6, and 5 ng/ml IL-10. The cells were first exposed to human IgE specific for gp120 and the bispecific antibody before exposure to ovalbumin-conjugated gp120 peptide. The bispecific antibody was assayed at concentrations of 0.3, 1, 3, 10, 30, and 100 µg/ml, as shown in FIG. 7. Nine week old cultured mast cells (5×10$^4$ cells per treatment) were first treated with human IgE (10 µg/ml) for 1 hour at 37° C., then washed and incubated with bispecific antibody at the indicated concentration, parental antibodies E10.10.3 (E.10, 10 µg/ml) or AT.10 (10 µg/ml), or a control antibody, anti-CD81 (10 µg/ml), for 20 minutes at 37° C. The cells were then challenged with ovalbumin-conjugated gp120 peptide for 1 hour at 37° C., and the amount of histamine release was then measured in the supernatant. All concentrations of bispecific antibodies showed an inhibitory effect on mast cell degranulation, ranging from 50 to 75% inhibition (see FIG. 7, lanes 3–8). Similar inhibitory results were seen in a duplicate experiment. The parental antibodies (either E.10.10.3 or AT.10) did not show significant inhibition (See FIG. 7, lanes 9 and 11). As expected, human IgE with the bispecific antibody did not influence histamine release (data not shown).

Figure 8:
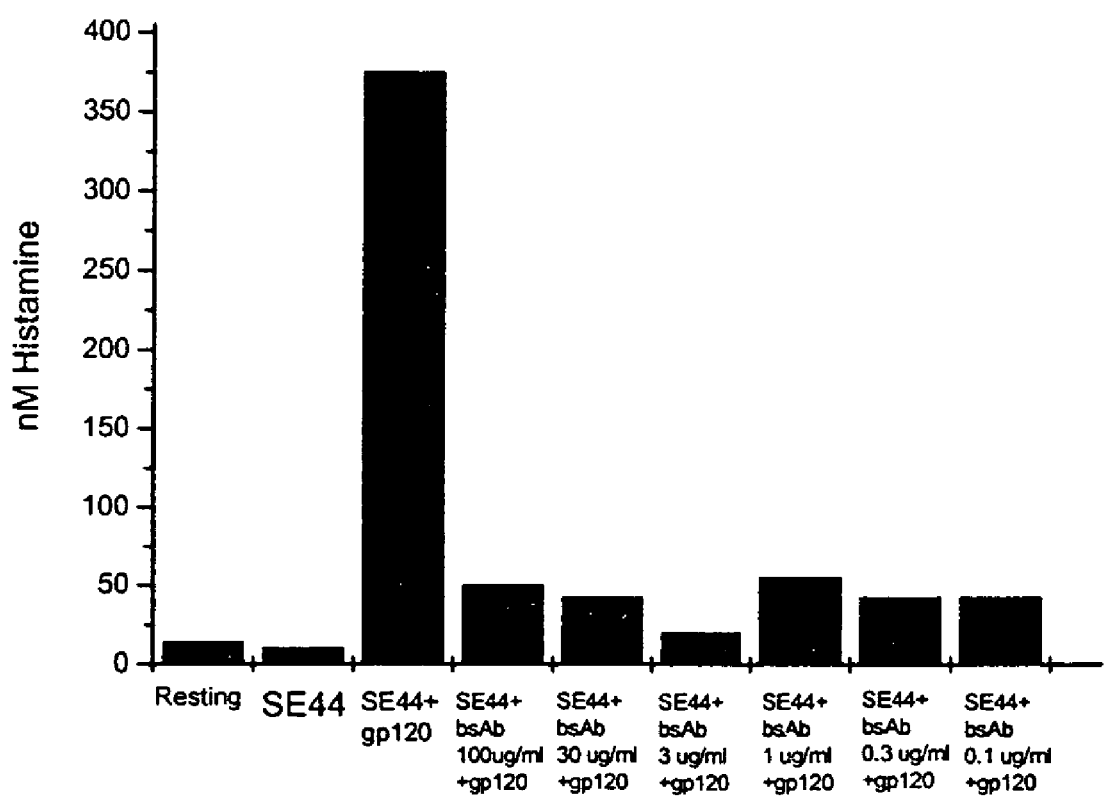
FIG. 8 shows the inhibition of histamine release by bispecific antibody on human cultured basophils. Basophils cultured from human cord blood were exposed to human IgE expressed from clone SE44 and then incubated with varying concentrations of bispecific antibody. When challenged with antigen, a greater than 60% inhibition of histamine release was seen at concentrations as low as 0.1 μg/ml of bispecific antibody.

Inhibition of histamine release by the bispecific antibody was also demonstrated in human cord blood basophils. Inhibition was shown with antibody concentrations from 0.3 to 100 µg/ml (see FIG. 8). Four week old basophils cultured in the presence of hIL-3 (1 ng/ml) and TGF-β (10 ng/ml) (5×10$^4$ cells per treatment) were first exposed to human IgE (clone SE44, 10 µg/ml) for 1 hour at 37° C., then washed and incubated with bispecific antibody at the indicated concentrations for 20 minutes at 37° C. The cells were then exposed to ovalbumin-conjugated gp120 peptide for 1 hour at 37° C. Histamine release was measured in the supernatant. A greater than 60% inhibition was observed at a concentration as low as 0.1 µg/ml of the bispecific antibody (See FIG. 8, lanes 4–9). This implies that the inhibitory (ITIM) pathway is dominant over the stimulatory (ITAM) pathway for this cell type.

Figure 9:
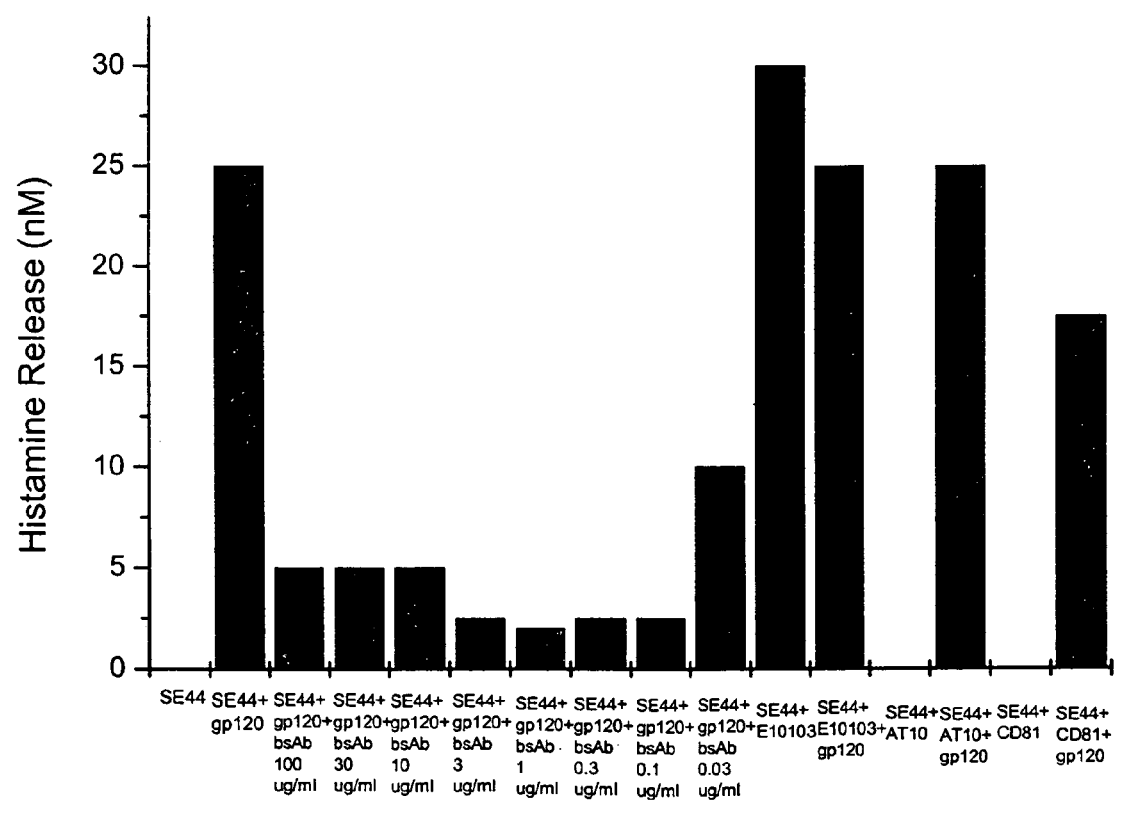

Inhibition of histamine release was also measured in basophils from human blood PBMC using the bispecific antibody (see FIG. 9). Human buffy coat was ficoll-separated and the leukocyte-enriched fraction was collected. Mixed leukocytes, which included circulating basophils (1×10$^5$ cells per treatment) were first exposed to human IgE (clone SE44, 10 µg/ml) for 1 hour at 37° C., then washed and incubated with either the bispecific antibody at the indicated concentration or one of the parental antibodies, E10.10.3 (10 µg/ml) or AT10 (10 µg/ml), for 20 minutes at 37° C. The cells were then exposed to ovalbumin-conjugated gp120 peptide for 1 hour at 37° C. before histamine release was measured in the supernatant. A known amount of exogenous human IgE (clone SE44, 10 µg/ml) was used to bind the "unoccupied" IgE receptors on the cell surface and then exposed to ovalbumin-conjugated gp120 peptide, in the presence of the bispecific antibody. A greater than 60% inhibition was observed at concentrations as low as 0.03 µg/ml (See FIG. 9, lane 10). The control parental antibody, AT.10, alone did not show any inhibitory effect (FIG. 9, lane 14).

A biphasic response with the bispecific antibody was observed. This response may be due to a stimulatory moiety of the bispecific antibody exerting its activatory effect at high concentrations (e.g. 100 µg/ml bispecific Ab, lanes 3–5), leading to less observable inhibition of histamine release. While at low concentration (e.g. 0.03 µg/ml bispecific antibody, lane 10), there is not enough ITAM/ITIM crosslinking to inhibit histamine release as significantly as seen in FIG. 9, lanes 6–9.

The bispecific molecule was then tested in cellular assays using human cultured mast cells for the inhibition of cytokine release, such as TNF-α. Human CD34$^+$ cells were cultured for 8 to 10 weeks in the presence of 80 ng/ml stem cell factor (SCF), 50 ng/ml IL-6 and 5 ng/ml IL-10 (Ochi et al., 1999). Nine week old cultured mast cells (5×10$^4$ cells per treatment) were first treated with human IgE (clone SE44, 10 µg/ml) for 1 hour at 37° C., then washed and incubated with or without bispecific Ab at the indicated concentration for 20 minutes at 37° C. The cells were then exposed to ovalbumin-conjugated gp120 peptide for 2 and 24 hours at 37° C. before TNF-α release was measured in the supernatant. At two hours there is very little TNF-α present in the supernatant of any of the samples. Results suggest that it takes 24 hours for TNF-α to be secreted into the supernatant.

The bispecific antibody was tested at 1 and 0.1 µg/ml. Inhibition of TNF-α release is most pronounced at 1 µg/ml after 24 hours (see FIG. 10). This demonstrates that in addition to histamine release, the ITAM/ITIM crosslinking also can inhibit cytokine release.

The examples and terms and expressions used above are exemplary only and not limiting, and the invention is defined only in the claims that follow, and includes all equivalents of the subject matter of the claims.

We claim:

1. A bispecific antibody, or a binding fragment thereof, comprising a first determinant that binds to an Immunoreceptor Tyrosine-Based Activation Module (ITAM), wherein said ITAM is selected from the group consisting of BCR, FcεRI, FcγRI, FcγRIIA, FcγRIIIA, and TCR, and a second determinant that binds to an Immunoreceptor Tyrosine-Based Inhibition Module (ITIM), wherein the ITIM is FcεRII.

2. The bispecific antibody of claim 1, wherein at least one determinant is humanized, human, chimeric, or an ScFv.

3. A method of inhibiting the release of TNF-α from a mast cell or a basophil comprising administering the bispecific antibody, or a binding fragment thereof, of claim 1, wherein said ITAM is FcεRI, FcγRI, FcγRIIA, or FcγRIIIA.

4. A method of inhibiting the release of histamine from a mast cell or a basophil comprising administering the bispecific antibody, or a binding fragment thereof, of claim 1, wherein said ITAM is FcεRI, FcγRI, FcγRIIA, or FcγRIIIA.

5. A method of ameliorating an allergic disease or condition in a mammal comprising administering the bispecific antibody, or a binding fragment thereof, of claim 1.

6. The method of claim 5, wherein the bispecific antibody is administered at a concentration range from 0.1 to 1 μg/ml.

7. A composition comprising the bispecific antibody, or a binding fragment thereof, of claim 1, and a physiologically acceptable carrier, excipient, or diluent.

8. A method of ameliorating an allergic disease or condition in a mammal comprising administering the composition of claim 7.

9. A method of inhibiting the release of TNF-α from a mast cell or a basophil comprising administering the composition of claim 7, wherein said ITAM is FcεRI, FcγRI, FcγRIIA, or FcγRIIIA.

10. A method of inhibiting the release of histamine from a mast cell or a basophil comprising administering the composition of claim 7, wherein said ITAM is FcεRI, FcγRI, FcγRIIA, or FcγRIIIA.

* * * * *